United States Patent [19]

Kamatani et al.

[11] 4,443,597

[45] Apr. 17, 1984

[54] POLYISOCYANATES

[75] Inventors: Yoshio Kamatani; Noriaki Fujita, both of Osaka, Japan

[73] Assignee: Takeda Chemical Industries, Inc., Osaka, Japan

[21] Appl. No.: 445,581

[22] Filed: Nov. 30, 1982

Related U.S. Application Data

[63] Continuation of Ser. No. 269,961, Jun. 3, 1981, abandoned.

[30] Foreign Application Priority Data

Jun. 23, 1980 [JP] Japan ................................. 55-85486

[51] Int. Cl.$^3$ .......................................... C07D 273/04
[52] U.S. Cl. ..................................................... 544/67
[58] Field of Search ........................................... 544/67

[56] References Cited

U.S. PATENT DOCUMENTS 3,748,329 7/1973 Liebsch et al. ...................... 544/67

FOREIGN PATENT DOCUMENTS 49-15275 4/1974 Japan ................................... 544/67

Primary Examiner—John M. Ford
Attorney, Agent, or Firm—Antonelli, Terry & Wands

[57] ABSTRACT

Polyisocyanates having oxadiazinetrione rings obtained by reacting bis(isocyanatomethyl)cyclohexane, an oligomer thereof, an adduct thereof or a mixture of them with carbon dioxide. Said polyisocyanates have excellent properties as raw materials for the production of polyurethanes, because of their higher reactivity at lower temperature and better storage stability.

10 Claims, 2 Drawing Figures

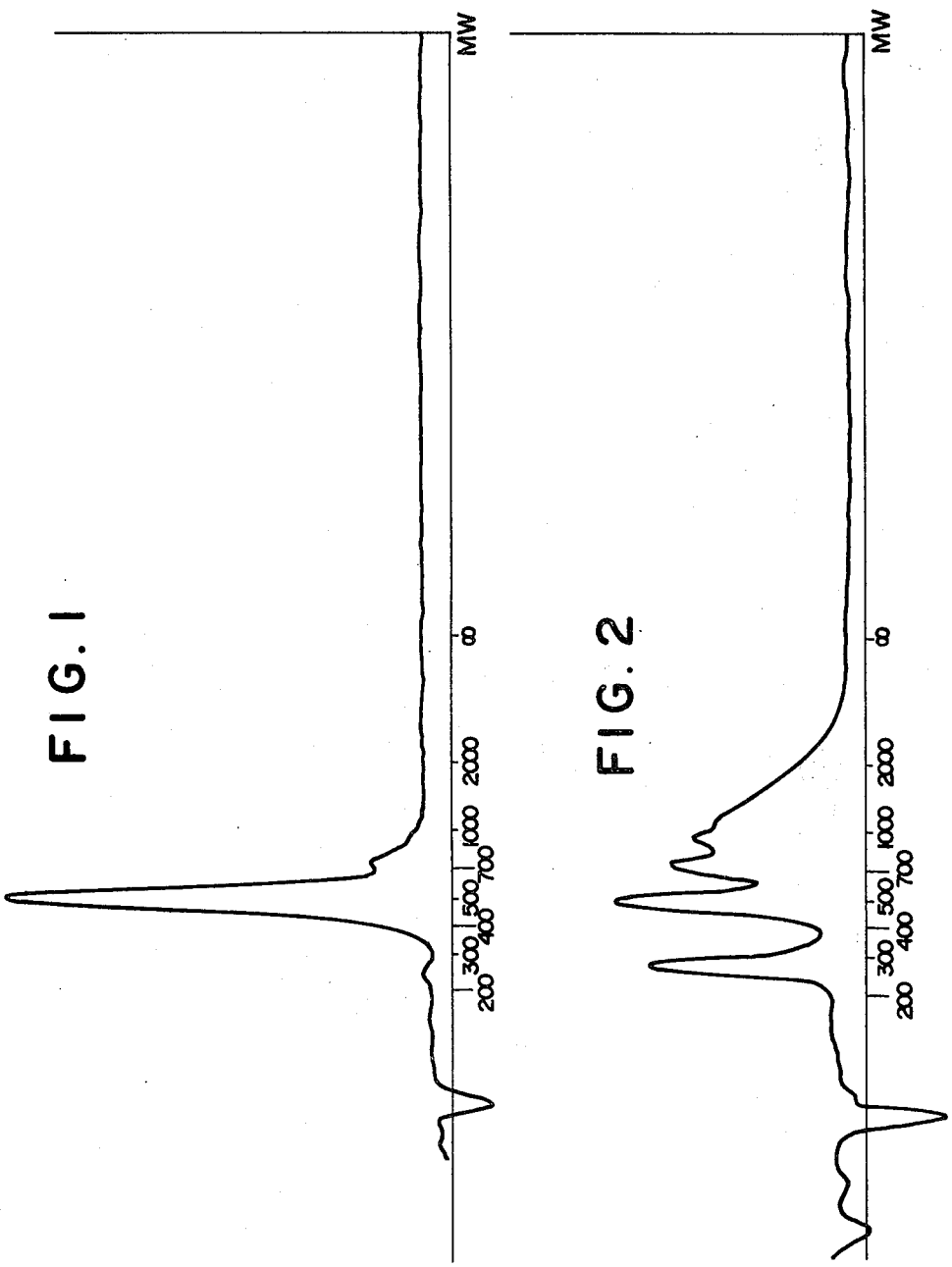

POLYISOCYANATES

This is a continuation of application Ser. No. 269,961, filed June 3, 1981, now abandoned.

This invention relates to polyisocyanates having oxadiazinetrione rings obtained by reacting bis-(isocyanatomethyl)cyclohexane, an oligomer thereof, an adduct thereof or mixtures thereof with carbon dioxide.

Heretofore, polyisocyanate having an oxadiazinetrione ring, useful for raw materials for polyurethanes, has been proposed, which is obtained by the reaction of an aliphatic or aromatic-aliphatic polyisocyanate with carbon dioxide (see British Pat. No. 1,145,952 and Derwent abstract JA-7343357-R). Polyisocyanates having the oxadiazinetrione ring derived, for example, from hexamethylene diisocyanate or xylylene diisocyanate have various limitations in the practical use as a starting material for polyurethanes. For instance, the oxadiazinetrione ring in these polyisocyanates requires a considerably high temperature in reacting the ring with polyhydroxy compounds to form allophanate linkages. Further, prepolymers obtained by converting the isocyanate groups of these polyisocyanates having oxadiazinetrione rings to urethanes or ureas are poor in stability in storage.

It is an object of the present invention to provide polyisocyanates having oxadiazinetrione ring which are more reactive even at lower temperatures and have superior storage stability.

Another object of the present invention is to provide polyisocyanates which can be employed even in the form of a mixture of polyisocyanates without purification after they are prepared, i.e., a crude form including even starting compound, for the preparation of polyurethane.

In the accompanying drawings,

FIGS. 1 and 2 are gel permeation chromatograms of the present polyisocyanates obtained by examples 1 and 3 below.

The present inventors have found that polyisocyanates having oxadiazinetrione ring which can be produced by reacting bis(isocyanatomethyl)cyclohexane with carbon dioxide, said bis(isocyanatomethyl)cyclohexane being one of alicyclic polyisocyanates which no attention has been drawn to, are superior to those obtained from an aliphatic or aromatic-aliphatic polyisocyanate and carbon dioxide, with respect to reactivity at lower temperature and storage stability. They have also found that the polyisocyanates obtained above have excellent properties as a starting material for various polyurethane resins.

According to the present invention, polyisocyanates having oxadiazinetrione rings are provided by reacting bis(isocyanatomethyl)cyclohexanes, oligomers thereof, adducts thereof or mixtures thereof with carbon dioxide.

Bis(isocyanatomethyl)cyclohexanes employable in this invention include cis and trans isomers of 1,4-bis(isocyanatomethyl)cyclohexane, 1,3-bis(isocyanatomethyl)cyclohexane or a mixture thereof.

Examples of oligomers from said diisocyanate are dimer or trimer. These can be prepared by bringing bis(isocyanatomethyl)cyclohexane into contact with a known dimerizing or trimerizing catalyst, such as tertiary amines, e.g., triethylamine, pyridine; tertiary phosphines, e.g., tributyl phosphine, dimethylphenylphosphine; metal salts of organic acid, e.g., calcium acetate, potassium acetate, sodium benzoate; sodium methoxide and other soluble metal compounds.

The adducts of bis(isocyanatomethyl)cyclohexane are reaction products of bis(isocyanatomethyl)cyclohexane with active hydrogen compounds such as prepolymers having terminal NCO group in such a conventional matter that excess NCO group is present. The active hydrogen compounds, one of reactants, are, for example, polyols, e.g., ethylene glycol, propylene glycol, diethylene glycol, 1,4-butanediol, glycerin, trimethylolpropane, polyether polyols, polyester polyols; or polyamino compounds, e.g., ethylenediamine, hexamethylenediamine, phenylenediamine, polyether polyamines.

Isocyanates such as those having the bis(isocyanatomethyl)cyclohexane skeleton above can be used in combination with other monoisocyanates and/or polyisocyanates. Further, the isocyanate groups of the bis(isocyanatomethyl)cyclohexane can partially be blocked with blocking agents.

The reaction of bis(isocyanatomethyl)cyclohexanes, oligomers thereof, adducts thereof, or mixtures thereof [hereafter simply referred to as bis(isocyanatomethyl)cyclohexane] with carbon dioxide proceeds, usually, in the presence of a catalyst. Examples of the catalysts, which are especially effective, are such tertiary phosphorus compounds as triethylphosphine, tri-n-butylphosphine, dimethylphenylphosphine, diethylcyclohexylphosphine, 1-ethylphospholane or 1-n-butylphosphane. Alternatively, such arsinc compounds as tri-n-butylarsine or triphenylarsine oxide, and such hydroquinones as hydroquinone and anthrahydroquinone may also be used. An amount of the catalyst used varies in the range of about 0.001–10 weight %, preferably about 0.01–3 weight % depending on the catalyst and reaction conditions employed.

Any form of carbon dioxide can be introduced as long as even a part can be dissolved in the reaction mixture. For example, carbon dioxide gas may be bubbled into the reaction mixture, solid carbon dioxide may be charged directly, or gaseous or liquefied carbon dioxide can be introduced under pressure. The reaction is carried out in the presence or absence of a solvent. Any solvent can be used, as long as it does not interfere with the reaction, e.g., cyclohexane, toluene, ethyl acetate, methyl ethyl ketone, tetrahydrofuran, cellosolve acetate, etc. It is sometimes advantageous to add a solvent in the course of the reaction, because viscosity of the reaction system increases with the progress of the reaction.

The reaction temperature varies normally from −70° C. to +150° C. depending upon the catalyst used. However, the temperature is preferably in the range of −40° C. to +70° C., especially −20° C. to 40° C., because side reactions of isocyanates, e.g. polymerization, often occur at high temperatures.

The reaction product obtained can be identified by IR and NMR analyses to be polyisocyanates having oxadiazinetrione rings. The product is a mixture of polyisocyanates usually having one to several (generally 2–5) oxadiazinetrione rings per molecule. It further includes some unreacted polyisocyanate. Degree (%) of conversion can be controlled by the amounts of carbon dioxide and the catalyst, reaction time and temperature etc. When the reaction has proceeded to a given degree, it can be terminated by stopping the supply of carbon dioxide and adding a reaction-terminating agent. The molecular weight of the product can be controlled over a broad range from low molecular weight to high molecular weight by setting the reaction period properly. The degree of reaction can be detected by such methods as determining the content of NCO groups, comparing the NMR peak of the H atom bound to the C atom adjacent to NCO and that of the H atom bound to the C atom adjacent to the oxadiazinetrione ring, measuring the viscosity of the reaction mixture or a chromatographic analysis of a residual amount of starting organic isocyanate. Examples of said terminating agent are bromoacetic acid esters, trichloroacetic acid, 2,4-dinitrophenol, cyanoacetic acid esters, dimethyl sulfate, boron trifluoride etherate, benzoyl chloride, methanesulfonic acid and methyl iodide.

The product of this invention which is produced from, for example, bis(isocyanatomethyl)cyclohexane is a polyisocyanate having an oxadiazinetrione ring having the following formula:

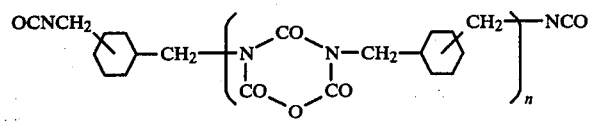

[wherein n is an integer of 1, 2, 3, 4 . . . . ] The product of this invention is a mixture of polysiocyanates having various values for n. In case this product is used for the production of a polyurethane, the product should desirably have an average of n of 0.01 to 5, preferably 0.1 to 3.

The polyisocyanate having an oxadiazinetrione ring, if necessary, can be separated from the unreacted monomeric polyisocyanate by such separation procedures an distillation, extraction, etc. Low and high molecular weight fractions can also be separated from each other by the procedures above. However, the crude mixture containing compounds of various molecular weights including monomer may be used as a starting material for producing polyurethanes. The polyisocyanate of the above formula wherein n is 1 or the crude product containing this compound is one of the desirable products of the present invention.

The product of this invention has two different types of functional groups, i.e. oxadiazinetrione ring and isocyanate group. Therefore this product is employable not only as an isocyanate for the production of polyurethane resins by reaction with active hydrogen compounds but also as a chain extender or a crosslinker for polyamino or polyhydroxy compounds by using the reactivity of the oxadiazinetrione ring with amino or hydroxyl compounds. Furthermore, a self-crosslinking polymer can be produced by reacting the isocyanate group with a polyfunctional active hydrogen compound to give an active hydrogen-terminated prepolymer whose terminal active hydrogen is reactive with the oxadiazinetrione ring. These products can broadly be used as materials for adhesives, coatings, moldings, foams, other resins which all can perform as same as polyurethane.

The oxadiazinetrione ring derived from bis-(isocyanatomethyl)cyclohexane has a feature that it reacts with hydroxy compounds at temperatures lower by about 20° C. than the reaction temperature of the trione rings derived from hexamethylene diisocyanate or xylylene diisocyanate. Such catalysts as tertiary amines, inorganic salts of metals, or organometallic compounds can accelerate this reaction. In such catalystic reaction, the oxdiazinetrione ring from bis-(isocyanatomethyl)cyclohexane can also react at lower temperature. Furthermore, the polyurethanes having oxadiazinetrione ring derived from bis(isocyanatomethyl)cyclohexane, which are usable as chain extender, crosslinker or self-crosslinking prepolymers have better solubilities and longer shelf lives than those derived from hexamethylene diisocyanate or xylylene diisocyanate. From this aspect, the present isocyanates have a greater practical value.

For fuller understanding of this invention, example are given below.

EXAMPLE 1

While introducing carbon dioxide gas at 0° C. at the rate of 100 ml/min. into 97 g of 1,3-bis(isocyanatomethyl)cyclohexane (a mixture of cis- and trans isomer), the reaction was allowed to proceed for 4 hours under stirring with the addition of 0.4 g of tri-n-butyl phosphine. The reaction was terminated by suspending the $CO_2$ gas feed and by adding 0.3 g of dimethyl sulfate. The reaction mixture showed a weight increase of 2.6 g and contained 36.6% of NCO. After removing the unaltered monomers by passing through a thin film evaporator, 26.5 g of a pale yellow viscous liquid was obtained which contained 18.9% of NCO and less than 1% of monomers. This liquid product (5 g) was dissolved in 10 ml of ethyl acetate, followed by adding 0.76 g of methanol and 0.3 mg of dibutyltin dilaurate. The reaction was conducted at 60° C. for 2 hours, whereupon the NCO groups disappeared. Then, the reaction mixture was evaporated to dryness. The gel permeation chromatogram of the resultant product is shown in FIG. 1. The product was treated by column chromatography on 300 g of silica gel. From the eluate obtained with a 85:15 mixture of chloroform and ethyl acetate, a resinous substance was obtained after evaporating the solvent. The IR spectrum of this product showed the absorptions at 3350 and 1710 cm$^{-1}$ which are assigned to the urethane linkage and at 1825, 1755 and 1720 cm$^{-1}$ which are assigned to the oxadiazinetrione ring. Further, gel permeation chromatographic assey of this product exhibits a single peak for molecular weight of about 500 (calcd.: 496). Based on the NMR spectrum given below and the results of elemental analysis, this product was confirmed to have the following structure.

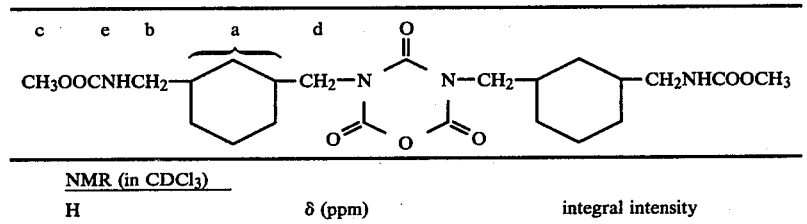

NMR (in CDCl$_3$)

| H | δ (ppm) | integral intensity |

-continued $$CH_3OOCNHCH_2 \underbrace{\overset{c\;\;e\;\;b\;\;\;\;\;a}{\text{—⟨cyclohexane⟩—}}} CH_2-N\overset{d}{\underset{\underset{O}{\overset{\|}{C}}}{\underset{\|}{\underset{O}{\big\backslash}}}}\overset{O}{\overset{\|}{C}}N-CH_2-\text{⟨cyclohexane⟩}-CH_2NHCOOCH_3$$

| | | |
|---|---|---|
| a | 0.5–2.1 | 20 |
| b | 2.8–3.2 | 4 |
| c | 3.6 | ⎱ |
| | | 10 |
| d | 3.5–3.9 | ⎰ |
| e | 4.8 | 2 |

| Elemental analysis | C | H | N |
|---|---|---|---|
| Calculated | 55.63 | 7.31 | 11.28 |
| Found | 55.73 | 7.10 | 11.35 |

EXAMPLE 2

While introducing carbon dioxide gas at 10° C. at the rate of 500 ml/min. into 582 g of 1,3-bis(isocyanatomethyl)cyclohexane, the reaction was allowed to proceed under stirring with the addition of 6.0 g of tri-n-butylphosphine. After 8 hours, the carbon dioxide feed was suspended and 5.0 g of dimethyl sulfate was added so as to terminate the reaction. The product was a viscous liquid, the weight of which was greater by 59 g than the original weight of the reaction system and the NCO content of which was 19.4%. The IR and NMR spectra of the composition revealed the presence of polyisocyanates having oxadiazinetrione structure.

EXAMPLE 3

A 300 ml-autoclave was charged with 97 g of 1,4-bis-(isocyanatomethyl)cyclohexane, and $CO_2$ gas was introduced under stirring. Then, 0.4 g of triethylphosphine was added thereto and the reaction was carried out at 35° C. and at a constant $CO_2$ pressure of 2 to 3 kg/cm². After 6 hours, the $CO_2$ gas pressure was released and 0.3 g of ethyl bromoacetate was added to the reaction mixture to terminate the reaction. The NCO content of the reaction mixture was 20.7%. The IR and NMR spectra of this product proved the production of polyisocyanates having oxadiazinetrione structure. Further, a gel permeation chromatographic assey of methylurethane derivative of this product shows some peaks of compounds corresponding to n=0, 1, 2, 3 and 4, respectively (FIG. 2).

EXAMPLE 4

To 194 g of 1,3-bis(isocyanatomethyl)cyclohexane was added a mixture of 0.04 g of a 40% solution of trimethylbenzylammonium hydroxide in methanol and 4 g of butyl acetate, and the reaction was conducted at room temperature for 3 hours. The reaction was terminated by adding 0.2 g of benzoyl chloride. The reaction mixture contained 39.0% of NCO (before reaction; 43.2%). The IR absorption at 1690 cm⁻¹ indicated the formation of isocyanurate rings. While introducing $CO_2$ gas into this mixture at 20° C., to which 1.4 g of tri-n-butylphosphine was added, and the mixture was allowed to react for 4 hours. After substituting the $CO_2$ with $N_2$, the reaction was terminated by adding 1.2 g of dimethyl sulfate. The product contained 25.9% of NCO. The IR and NMR spectra of this product attested the presence of both oxadiazinetrione and isocyanurate rings.

EXAMPLE 5

194 g of 1,3-bis(isocyanatomethyl)cyclohexane and 11.8 g of 1,6-hexanediol were allowed to react at 80° C. for 3 hours with stirring. After the reaction mixture was cooled to 30° C., $CO_2$ gas was bubbled into the mixture and 0.8 g of triethylphosphine was added thereto. The mixture was allowed to react for 6 hours. Then, the $CO_2$ gas feed was suspended and 0.6 g of ethyl bromoacetate was added so as to terminate the reaction. The product contained 21.7% of NCO. The IR and NMR spectra of this product showed the presence of both urethane linkage and oxadiazinetrione ring.

REFERENCE EXAMPLE 1

To 168 g of hexamethylenediisocyanate was introduced $CO_2$ gas at the rate of 300 ml/min. at 50° C., to which 1.2 g of tri-n-butylphosphine was added. The mixture was allowed to react for 6 hours with stirring. Then, the $CO_2$ gas feed was suspended and 1.0 g of dimethyl sulfate was added so as to terminate the reaction. The weight of the product was treater by 22 g than the original weight of the reaction system. The product contained 20.2% of NCO. The IR and NMR spectra of this product showed that this product was a polyisocyanate having oxadiadinetrione ring.

REFERENCE EXAMPLE 2

94 g of m-xylylenediisocyanate and 0.2 g of tri-n-butylphosphine were allowed to react at room temperature as in Reference Example 1. After 8 hours, the weight of the product was greater by 8.8 g than the original weight of the reaction system and the product contained 22.8% of NCO.

EXAMPLE 6

Each of the reaction products obtained in Examples 2 to 4 and Reference Example 1 was mixed with a polyol component, diluted with a solvent and sprayed on a cold rolled steel panel, followed by heating for 20 minutes to produce a film about 40μ thick. The curable temperatures and the properties of films are indicated in Table I.

TABLE I

| | Example 2 | Example 3 | Example 4 | Reference Example 1 | Example 2 | Example 3 | Reference Example 1 |
|---|---|---|---|---|---|---|---|
| Polyisocyanates | 10 | 10 | 10 | 10 | 10 | 10 | 10 |

TABLE I-continued

|  | Example 2 | Example 3 | Example 4 | Reference Example 1 | Example 2 | Example 3 | Reference Example 1 |
|---|---|---|---|---|---|---|---|
| (parts by wt.) |  |  |  |  |  |  |  |
| Polyol component | Acrydic A-801* | Acrydic A-801* | Acrydic A-801* | Acrydic A-801* | Takelac U-25** | Takelac U-25** | Takelac U-25** |
| (parts by wt.) | 75 | 77 | 69 | 83 | 27 | 27 | 29 |
| Curable temperature (°C.) | 140 | 140 | 140 | 160 | 140 | 140 | 150 |
| Solvent resistance of cured film | excellent | excellent | excellent | good | good | good | fair |

*Acrylic polyol, OH Value: 50, Non-volatile matter: 50%, manufactured by Dainippon Ink and Chemicals Inc.
**Polyesterpolyol, OH Value: 141, Non-volatile matter: 75%, manufactured by Takeda Chemical Industries, Ltd.

EXAMPLE 7

15 g of the polyisocyanates obtained in Example 2 was dissolved in 10 g of cellosolve acetate and was allowed to react with 7.5 g of triethylene glycol in the presence of 1 mg of dibutyltin dilaurate at 70° C. for 3 hours. The IR analysis of the resultant prepolymers showed a substantially complete disappearance of NCO groups on the one hand and that the oxadiazinetrione ring of the starting material remained unchanged on the other hand. Instead of using the polyisocyanate of Example 2, prepolymers having no NCO groups were prepared in the same manner by using 13.5 g of the polyisocyanate of Reference Example 1 and by using 13.6 g, of the polyisocyanate of Reference Example 2, respectively. Using these prepolymers, curing tests were carried out at various temperatures. Each of these prepolymers was coated on glass plates with or without 0.03% of 1,3-diacetoxytetrabutyldistannoxane as a curing catalyst and cured under various temperatures for 20 minutes. The 2-week, room-temperature storage stability data on these prepolymers are also given in Table II.

TABLE II

| Polyisocyanate | Example 2 | | Reference Example 1 | | Reference Example 2 | |
|---|---|---|---|---|---|---|
| Curing catalyst | 0 | 0.03% | 0 | 0.03% | 0 | 0.03% |
| Curable temperature | 150° C. | 140° C. | 170° C. | 160° C. | 170° C. | 160° C. |
| Storage stability | Clear | Clear | Turbid | Turbid | Turbid | Turbid |

We claim:

1. A polyisocyanate having an oxadiazinetrione ring, represented by the formula:

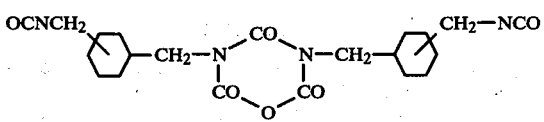

2. A polyisocyanate having an oxadiazinetrione ring which is represented by the following generic formula:

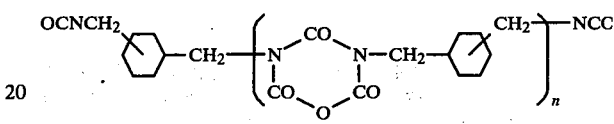

wherein an average of n is 0.01 to 5 and which is obtained by reacting bis(isocyanatomethyl)cyclohexane with carbon dioxide at a temperature ranging from −40° C. to 70° C.

3. A polyisocyanate having an oxadiazinetrione ring according to claim 2, wherein the temperature is from −20° C. to 40° C.

4. A polyisocyanate having an oxadiazinetrione ring according to claim 2, wherein the average of n is 0.1 to 3.

5. A polyisocyanate having an oxadiazinetrione ring according to claim 2, wherein the average of n is 0.1 to 3 and the temperature is from −20° C. to 40° C.

6. A polyisocyanate-containing material which comprises a reaction product obtained by reacting bis(isocyanatomethyl)cyclohexane with carbon dioxide at a temperature ranging from −40° C. to 70° C., said reaction product consisting essentially of at least one polyisocyanate having an oxadiazinetrione ring and being represented by the formula:

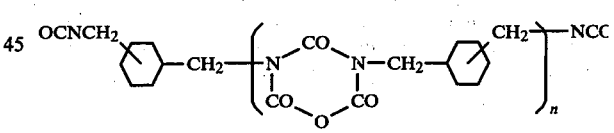

wherein an average of n is 0.01 to 5.

7. A polyisocyanate-containing material according to claim 6, wherein said reaction product consists essentially of a polyisocyanate in which n is 1.

8. A polyisocyanate-containing material according to claim 6, wherein the temperature is from −20° C. to 40° C. and the average of n is 0.1 to 3.

9. A polyisocyanate-containing material according to claim 6, wherein the temperature is from −20° C. to 40° C.

10. A polyisocyanate-containing material according to claim 6, wherein the average of n is 0.1 to 3.

* * * * *